(12) United States Patent
Silberman et al.

(10) Patent No.: US 11,017,323 B2
(45) Date of Patent: May 25, 2021

(54) METHOD AND APPARATUS FOR IMPROVING A PROFILE ANALYSIS OF AN INTERPRETIVE FRAMEWORK BASED ON DIGITAL MEASUREMENT OF THE PRODUCTION OF AND RESPONSES TO VISUAL STIMULI

(71) Applicant: Psymark LLC, La Crescenta, CA (US)

(72) Inventors: Karen Sue Silberman, Glendale, CA (US); Roxanne Elizabeth Helm-Stevens, West Covina, CA (US); Dana Louise Khudaverdyan, Glendale, CA (US); John Randy Fall, San Gabriel, CA (US); David Sevak Khudaverdyan, Glendale, CA (US)

(*) Notice: Subject to any disclaimer, the term of this patent is extended or adjusted under 35 U.S.C. 154(b) by 792 days.

(21) Appl. No.: 15/002,392

(22) Filed: Jan. 20, 2016

(65) Prior Publication Data

US 2016/0217394 A1 Jul. 28, 2016

Related U.S. Application Data

(60) Provisional application No. 62/107,366, filed on Jan. 24, 2015.

(51) Int. Cl.
*G06N 20/10* (2019.01)
*G16H 50/20* (2018.01)
(Continued)

(52) U.S. Cl.
CPC ............ *G06N 20/10* (2019.01); *A61B 5/168* (2013.01); *A61B 5/7264* (2013.01); *G06N 20/00* (2019.01); *G16H 50/20* (2018.01); *A61B 5/6898* (2013.01)

(58) Field of Classification Search
CPC .... G06N 99/005; G16H 50/20; A61B 5/7264; A61B 5/6898; G06F 19/00
See application file for complete search history.

(56) References Cited

U.S. PATENT DOCUMENTS

| | | | |
|---|---|---|---|
| 6,473,639 | B1 | 10/2002 | Fischell et al. |
| 8,401,609 | B2 | 3/2013 | Deisseroth et al. |
| | | (Continued) | |

FOREIGN PATENT DOCUMENTS

| | | |
|---|---|---|
| EP | 1385426 B1 | 4/2004 |
| WO | 2012149607 A1 | 11/2012 |
| WO | 2013071285 A1 | 5/2013 |

OTHER PUBLICATIONS

Inzelberg et al ("Visuo-Motor Coordination Deficits and Motor Impairments in Parkinson's Disease", PLoS ONE 3(11): e3663, Nov. 6, 2008, pp. 1-8) (Year: 2008).*

(Continued)

*Primary Examiner* — Kakali Chaki
*Assistant Examiner* — Robert Lewis Kulp
(74) *Attorney, Agent, or Firm* — Seyfarth Shaw LLP

(57) ABSTRACT

A method for improving a profile analysis of an interpretive framework stored in a memory may include producing and displaying visual stimuli on a computerized device to test visual and visual motor responses of an individual subject in response to the displayed visual stimuli. The method may also include classifying and categorizing digitally measured visual and visual motor responses of the individual subject to the displayed visual stimuli. The method may further include continually modifying parameters of the profile analysis of the interpretive framework corresponding to at least one condition based at least in part on an item analysis corresponding to a pattern of performance determined during the classifying and categorizing of the digitally mea- (Continued)

sured visual and visual motor responses of the individual subject.

21 Claims, 10 Drawing Sheets

(51) Int. Cl.
*G06N 20/00* (2019.01)
*A61B 5/00* (2006.01)
*A61B 5/16* (2006.01)

(56) References Cited

U.S. PATENT DOCUMENTS

| | | | |
|---|---|---|---|
| 8,473,043 | B1 | 6/2013 | Modarres |
| 8,509,884 | B2 | 8/2013 | Snyder |
| 9,443,205 | B2* | 9/2016 | Wall ............... G06F 19/3418 |
| 10,383,553 | B1* | 8/2019 | Glenn ................... A61B 5/16 |
| 2005/0228236 | A1 | 10/2005 | Diederich et al. |
| 2006/0136806 | A1 | 6/2006 | Harris et al. |
| 2013/0261490 | A1 | 10/2013 | Truccolo et al. |
| 2014/0057244 | A1* | 2/2014 | Roots .................. G09B 7/00 434/362 |
| 2014/0304200 | A1* | 10/2014 | Wall ................. G16H 50/20 706/12 |
| 2014/0330159 | A1* | 11/2014 | Costa ............... A61B 5/1124 600/558 |
| 2014/0336539 | A1* | 11/2014 | Torres ................ A61B 5/11 600/595 |
| 2015/0305686 | A1* | 10/2015 | Coleman ........... A61B 5/7264 600/301 |

OTHER PUBLICATIONS

Muzzafar Bashir ("A Novel Multisensoric System Recording and Analyzing Human Biometric Features for Biometric and Biomedical Applications", Dissertation, University of Regensburg, Germany, 2010, pp. 1-131) (Year: 2010).*

Muzaffar Bashir ("A Novel Multisensoric System Recording and Analyzing Human Biometric Features for Biometric and Biomedical Applications", University of Regensburg, Dec. 2010, pp. 1-125), (Year: 2010).*

Tseng, Po-He, et al. "High-throughput classification of clinical populations from natural viewing eye movements." Journal of neurology 260.1 (2013): 275-284.

Mueller, Andreas, et al. "Discriminating between ADHD adults and controls using independent ERP components and a support vector machine: a validation study." Nonlinear biomedical physics 5.1 (2011): 5.

Christop Lehmanna et al., "Application and Comparison of Classification Algorithms for Recognition of Alzheimer's Disease in electrical brain Activity (EEG)," Journal of Neuroscience Methods 171 (2007) 342-350.

Dietterich, T.G., & Bakiri, G., "Solving MultiClass Learning Problems via Error-Correcting Output Codes," (1995).

Lowe, D. G., "Distinctive Image Features From Scale-Invariant Keypoints," International Journal of Computer Vision, 60(2), pp. 91-110, (2004).

Smith, J.R. & Chang, S.F., "Local Color and Texture Extraction and Spatial Query," In Image Processing, 1996. Proceedings., International Conference on (vol. 3, pp. 1011-1014), IEEE, (1996).

Suykens, J.A. & Vandewalle, J., "Least Squares Support Vector Machine Classifiers," Neural Processing Letters, 9(3), pp. 293-300, (1999).

Quinlan, J.R., Book Review: "C4.5: Programs for Machine Learning," (vol. 1), Morgan Kaufmann, (1993).

* cited by examiner

METHOD AND APPARATUS FOR IMPROVING A PROFILE ANALYSIS OF AN INTERPRETIVE FRAMEWORK BASED ON DIGITAL MEASUREMENT OF THE PRODUCTION OF AND RESPONSES TO VISUAL STIMULI

CROSS-REFERENCE TO RELATED APPLICATION

This application claims the benefit under 35 U.S.C. § 119(e) to U.S. Provisional Patent Application No. 62/107,366, entitled "DIGITAL MEASUREMENT OF THE PRODUCTION AND RESPONSES OF VISUAL STIMULI," filed on Jan. 24, 2015, the disclosure of which is expressly incorporated by reference herein in its entirety.

BACKGROUND

1. Field

Certain aspects of the present disclosure generally relate to machine learning and, more particularly, to a method and apparatus for improving a profile analysis of an interpretive framework based on digital measurement of the production of and responses to visual stimuli.

2. Background

Mental disorders that can be diagnosed and begin in childhood (e.g., attention-deficit/hyperactivity disorder (ADHD), Tourette syndrome, behavior disorders, mood and anxiety disorders, autism spectrum disorders, substance use disorders, etc.) may be referred to as "childhood mental disorders." These mental disorders may be described as serious changes in the ways children learn, behave, or handle their emotions. Onset of symptoms may begin in early childhood, while symptoms of some disorders may develop in the teenage years. Diagnosis of the noted mental disorders may occur during school years or earlier.

Although rates of mental disorders among young people in America have been increasing steadily over the past half century, mental disorders of some children may go unrecognized. For example, school psychologists, clinical psychologists, physicians, researchers and others routinely use visual based assessments for children and adults to diagnose, treat or research visual, visual-motor integration, memory, cognition, attention, and neurological deficits. Assessment of visual, visual-motor integration, memory, cognition, attention, and neurological deficits may be indicative of various disabilities and medical conditions.

In particular, visual based assessments for children and adults may include correlations between visual-motor skill development and children with high functioning autism spectrum disorder, traumatic brain impairment and attention deficit/hyperactivity disorder, intellectual disorder, and Tourette Syndrome. Additionally, certain visual-motor drawing tasks have been beneficial in the identification and early screening of certain neurological disorders such as Parkinson's, Alzheimer's, and Mild Cognitive Impairment. Assessment instruments in current use, however, have significant weaknesses that limit their usefulness. For example, bias and manual errors may occur during measurements conducted using these assessment instruments.

SUMMARY

A method for improving a profile analysis of an interpretive framework stored in a memory may include producing and displaying visual stimuli on a computerized device to test visual and visual motor responses of an individual subject in response to the displayed visual stimuli. The method may also include classifying and categorizing digitally measured visual and visual motor responses of the individual subject to the displayed visual stimuli. The method may further include continually modifying parameters of the profile analysis of the interpretive framework corresponding to at least one condition based at least in part on an item analysis corresponding to a pattern of performance determined during the classifying and categorizing of the digitally measured visual and visual motor responses of the individual subject.

A method for a diagnostic profile analysis of an individual subject according to an interpretive framework stored in a memory may include digitally measuring visual and visual motor responses of the individual subject to visual stimuli displayed using a computerized device. The method may also include generating an item analysis corresponding to a pattern of performance determined from the digitally measured visual and visual motor responses of the individual subject. The method may further include providing an assessment of the individual subject based at least in part on a score of a condition correlation function corresponding to the item analysis of the pattern of performance determined from the digitally measured visual and visual motor responses of the individual subject.

An apparatus configured to improve a profile analysis of an interpretive framework, the apparatus may include a display, a memory configured to store the interpretive framework, and a processor(s) coupled to the display and the memory. The processor(s) may be configured to produce and to show visual stimuli on the display to test visual and visual motor responses of an individual subject in response to the displayed visual stimuli. The processor(s) may also be configured to classify and to categorize digitally measured visual and visual motor responses of the individual subject to the visual displayed stimuli. The processor(s) may be further configured to continually modify parameters of the profile analysis of the interpretive framework corresponding to at least one condition based at least in part on an item analysis corresponding to a pattern of performance determined during the classifying and categorizing of the digitally measured visual and visual motor responses of the individual subject.

A computer program product for a diagnostic profile analysis of an individual subject is also described. The computer program product may include a non-transitory computer readable medium having program code recorded thereon. The program code may include program code to digitally measuring visual and visual motor responses of the individual subject to visual stimuli displayed using a computerized device. The program code may also include program code to generating an item analysis corresponding to a pattern of performance determined from the digitally measured visual and visual motor responses of the individual subject. The program code may further include program code to provide an assessment of the individual subject based at least in part on a score of a condition correlation function corresponding to the item analysis of the pattern of performance determined from the digitally measured visual and visual motor responses of the individual subject.

This has outlined, rather broadly, the features and technical advantages of the present disclosure in order that the detailed description that follows may be better understood. Additional features and advantages of the disclosure will be described below. It should be appreciated by those skilled in the art that this disclosure may be readily utilized as a basis for modifying or designing other structures for carrying out the same purposes of the present disclosure. It should also be realized by those skilled in the art that such equivalent constructions do not depart from the teachings of the disclosure as set forth in the appended claims. The novel features, which are believed to be characteristic of the disclosure, both as to its organization and method of operation, together with further objects and advantages, will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

The features, nature, and advantages of the present disclosure will become more apparent from the detailed description set forth below when taken in conjunction with the drawings in which like reference characters identify correspondingly throughout.

DETAILED DESCRIPTION

Figure 1:
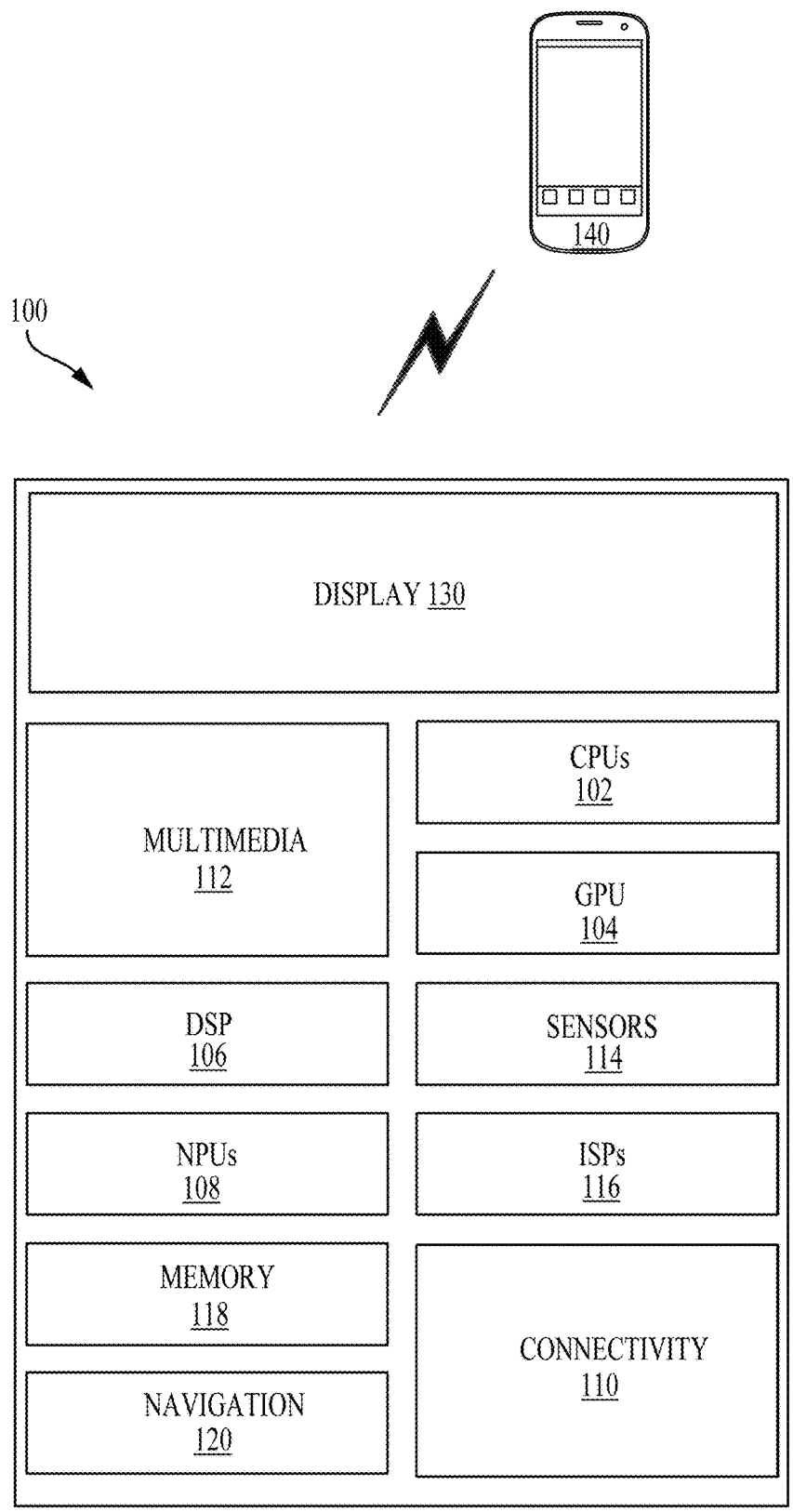
FIG. 1 illustrates an example implementation of designing a neural network using a computer system, including a general-purpose processor in accordance with certain aspects of the present disclosure.

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. It will be apparent to those skilled in the art, however, that these concepts may be practiced without these specific details. In some instances, well-known structures and components are shown in block diagram form in order to avoid obscuring such concepts.

Based on the teachings, one skilled in the art should appreciate that the scope of the disclosure is intended to cover any aspect of the disclosure, whether implemented independently of or combined with any other aspect of the disclosure. For example, an apparatus may be implemented or a method may be practiced using any number of the aspects set forth. In addition, the scope of the disclosure is intended to cover such an apparatus or method practiced using other structure, functionality, or structure and functionality in addition to or other than the various aspects of the disclosure set forth. It should be understood that any aspect of the disclosure disclosed may be embodied by one or more elements of a claim.

The word "exemplary" is used herein to mean "serving as an example, instance, or illustration." Any aspect described herein as "exemplary" is not necessarily to be construed as preferred or advantageous over other aspects.

Although particular aspects are described herein, many variations and permutations of these aspects fall within the scope of the disclosure. Although some benefits and advantages of the preferred aspects are mentioned, the scope of the disclosure is not intended to be limited to particular benefits, uses or objectives. Rather, aspects of the disclosure are intended to be broadly applicable to different technologies, system configurations, networks and protocols, some of which are illustrated by way of example in the figures and in the following description of the preferred aspects. The detailed description and drawings are merely illustrative of the disclosure rather than limiting, the scope of the disclosure being defined by the appended claims and equivalents thereof.

Mental disorders that can be diagnosed and begin in childhood (e.g., attention-deficit/hyperactivity disorder (ADHD), Tourette syndrome, behavior disorders, mood and anxiety disorders, autism spectrum disorders, substance use disorders, etc.) may be referred to as "childhood mental disorders." These mental disorders may be described as serious changes in the ways children learn, behave, or handle their emotions. Onset of symptoms may begin in early childhood, while symptoms of some disorders may develop in the teenage years. Diagnosis of the noted mental disorders may occur during school years or earlier.

Although rates of mental disorders among young people in America have been increasing steadily over the past half century, mental disorders of some children still go unrecognized. For example, school psychologists, clinical psychologists, physicians, researchers and others routinely use visual based assessments for children and adults to diagnose, treat or research visual, visual-motor integration, memory, cognition, attention, and neurological deficits. Assessment of these visual, visual-motor integration, memory, cognition, attention, and neurological deficits may be indicative of various disabilities and medical conditions.

For example, visual based assessments for children and adults may include correlations between visual-motor skill development and children with high functioning autism spectrum disorder, traumatic brain impairment and attention deficit/hyperactivity disorder, intellectual disorder, and Tourette Syndrome. Additionally, certain visual-motor drawing tasks have been beneficial in the identification and early screening of certain neurological disorders such as Parkinson's, Alzheimer's, and Mild Cognitive Impairment.

While conventional developmental tests may be psychometrically sound, these tests may offer only pencil and paper versions that are cumbersome and time consuming to score accurately. In particular, the scoring requires rulers and protractors, which can lead to errors. As a result, these assessment instruments have significant weaknesses that limit their usefulness. For example, bias and manual errors may occur during measurement conducted using the assessment instruments. Some other visual assessment instruments use computerized scoring but lack the capacity to use learning algorithms and neural networks to continually improve accuracy and predict potential disabilities and/or conditions.

An artificial neural network, which may comprise an interconnected group of artificial neurons (e.g., neuron models), is a computational device or represents a method to be performed by a computational device. For example, convolutional neural networks are a type of feed-forward artificial neural network. Convolutional neural networks may include collections of neurons that each has a receptive field and that collectively tile an input space. Convolutional neural networks (CNNs) have numerous applications. In particular, CNNs have broadly been used in the area of pattern recognition and classification.

Deep learning architectures, such as deep belief networks and deep convolutional networks, are layered neural networks. In deep learning architectures, the output of a first layer of neurons becomes an input to a second layer of neurons, the output of the second layer of neurons becomes an input to a third layer of neurons, and so on. These deep neural networks may be trained to recognize a hierarchy of features in an item analysis and thus, have been used in pattern recognition and other classification applications. Like convolutional neural networks, computation in these deep learning architectures may be distributed over a population of processing nodes, which may be configured in one or more computational chains. These multi-layered architectures may be trained one layer at a time and, for example, may be fine-tuned using back propagation.

Aspects of the present disclosure are related to improving a profile analysis of an interpretive framework based on digital measurement of the production of and responses to visual stimuli. The profile analysis includes measuring visual and visual motor responses of an individual subject to visual stimuli displayed using a computerized device. This aspect of the present disclosure may also classify and categorize the results of the measurements and make predictions about the possibility of various disorders or suggest other measures to investigate and rule out other possible conditions using learning algorithms and neural networks. This aspect of the present disclosure may include adjusting a condition correlation function over time based on digitally measuring responses to visual stimuli on a computerized device through the use of learning algorithms.

In one aspect of the disclosure a mobile device is used to assess visual motor skills, memory, attention, and other cognitive skills that may be indicative of various conditions. The measurements are then used to generate correlations to classify and categorize the results into various groups, initially indicating either a possible disorder/condition or no disorder. Additionally, results will be able, with increasing accuracy (learning algorithms), to predict various disorders/conditions as well as recommend additional areas of assessment to further investigate and rule out possible disorders/conditions. The various learning algorithms within a neural network may be configured on the mobile device or a server device according to aspects of the present disclosure.

FIG. 1 illustrates an example implementation of the aforementioned method of for improving a profile analysis of an interpretive framework based on digital measurement of the production of and responses to visual stimuli using a computer system 100 (e.g., a system on chip (SOC) and/or a server computer system). The computer system 100 may include a general-purpose processor or multi-core general-purpose processors (CPU) 102, in accordance with certain aspects of the present disclosure. Variables (e.g., neural signals and synaptic weights), system parameters associated with a computational device (e.g., neural network with weights), delays, frequency bin information, and task information may be stored in a memory block. The memory block may be associated with a neural processing unit (NPU) 108, a CPU 102, a graphics processing unit (GPU) 104, a digital signal processor (DSP) 106, a dedicated memory block 118, or may be distributed across multiple blocks. Instructions executed at the CPU 102 may be loaded from a program memory associated with the CPU 102 or may be loaded from a dedicated memory block 118.

The computer system 100 may also include additional processing blocks configured to perform specific functions, such as a GPU 104, a DSP 106, a connectivity block 110, which may include fourth generation long term evolution (4G LTE) connectivity, unlicensed Wi-Fi connectivity, USB connectivity, Bluetooth connectivity, and the like. In addition, a multimedia processor 112 in combination with a display 130 may, for example, classify and categorize the results of measurements of visual and visual motor responses of an individual subject to visual stimuli displayed using the display 130. In some aspects, the NPU 108 may be implemented in the CPU 102, DSP 106, and/or GPU 104. The computer system 100 may further include a sensor processor 114, image signal processors (ISPs) 116, and/or navigation 120, which may, for instance, include a global positioning system.

The computer system 100 may be based on an ARM instruction set or the like. In another aspect of the present disclosure, the computer system 100 may be server computer in communication with a mobile device 140. In this arrangement, the mobile device 140 may include and general-purpose processor and other features of the computer system 100. In this aspect of the present disclosure, instructions loaded into a general-purpose processor or neural processing unit of the mobile device 140 may include code for digitally measuring visual and visual motor responses of the individual subject to visual stimuli displayed using a display. The instructions loaded into the general-purpose processor may also include code for providing an assessment of the individual subject based at least in part on a score of a condition correlation function corresponding to an item analysis of a pattern of performance determined from the digitally measured visual and visual motor responses of the individual subject. The computer system 100 may determine a predicted condition of the individual subject when the score of the condition correlation function is within a predetermined range.

In an aspect of the present disclosure, the instructions loaded into the CPU 102 or the NPU 108 may include code for classifying and categorizing digitally measured visual and visual motor responses of an individual subject to visual stimuli displayed using the display 130. The instructions loaded into the CPU 102 may also include code for continually modifying parameters of the profile analysis of the interpretive framework corresponding to at least one condition based at least in part on an item analysis corresponding to a pattern of performance determined during the classifying and categorizing of the digitally measured visual and visual motor responses of the individual subject (e.g., in conjunction with the DSP 106 and/or the NPU 108). The instructions loaded into the CPU 102 may further include code for providing an assessment of the individual subject based at least in part on a score of a condition correlation function corresponding to the item analysis of the pattern of errors determined from the digitally measured visual and visual motor responses of the individual subject.

Figure 2:
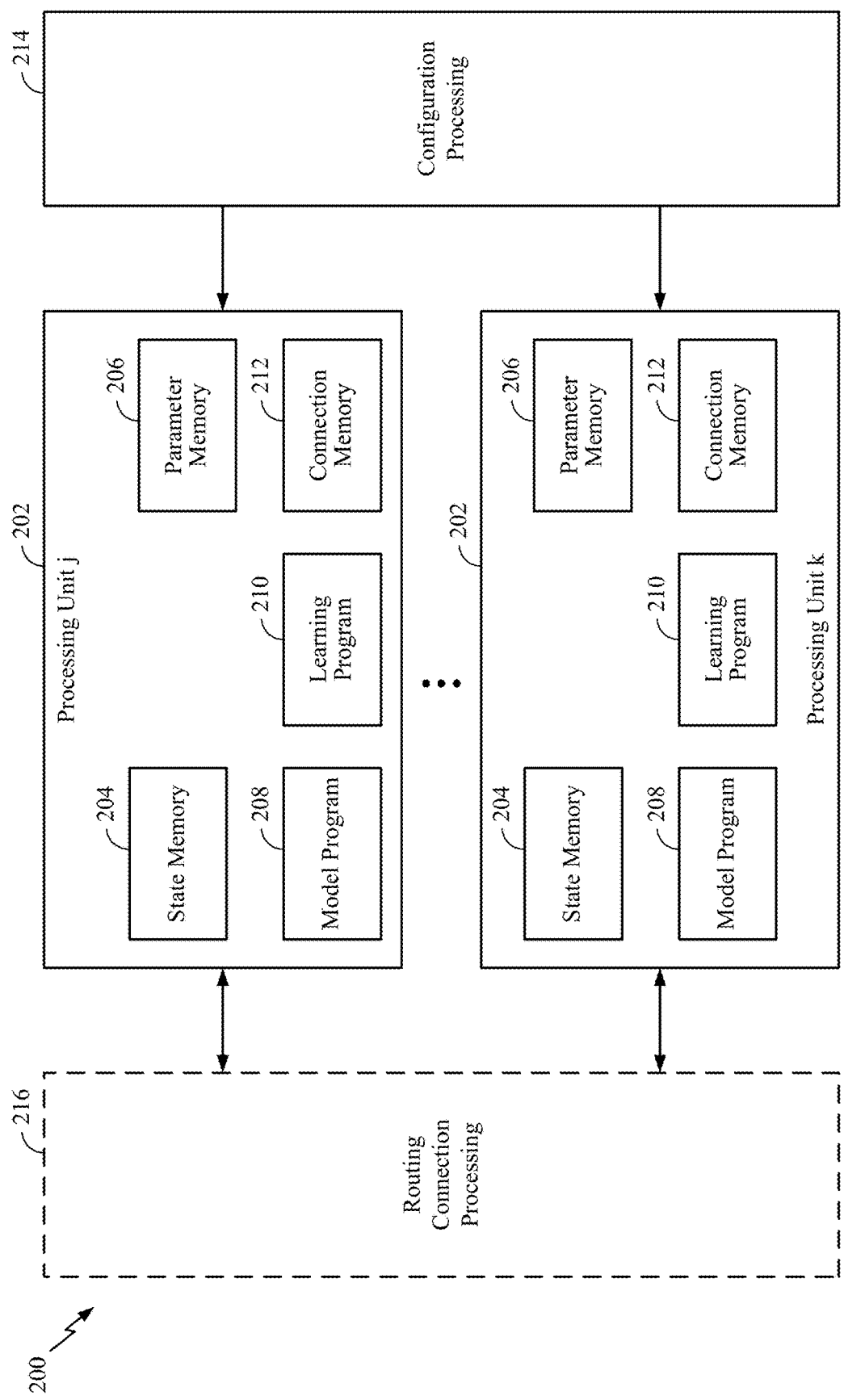
FIG. 2 illustrates an example implementation of a system in accordance with aspects of the present disclosure.

FIG. 2 illustrates an example implementation of a system 200 in accordance with certain aspects of the present disclosure. As illustrated in FIG. 2, the system 200 may have multiple processing units 202 that may perform various operations of methods described herein. Each of the multiple processing units 202 may comprise a state memory 204 and a parameter memory 206 that may store parameters of a neural network. In addition, each of the multiple processing units 202 may have a model program memory 208 for storing a model program, a learning program memory 210 for storing a local learning program, and a connection memory 212. Furthermore, as illustrated in FIG. 2, each of the multiple processing units 202 may interface with a configuration processing unit 214 for providing configurations for memories of the processing unit, and with a routing connection processing unit 216 that provides routing between the multiple processing units 202.

As discussed above, deep learning architectures may perform a condition recognition/classification task by learning to represent inputs at successively higher levels of abstraction in each layer, thereby building up a useful feature representation of the input data. In this way, deep learning may address a major bottleneck of traditional machine learning.

Locally connected neural networks may be well suited to problems in which the classification and categorization of inputs is meaningful. For instance, a network designed to recognize patterns of performance errors from an individual subject in response to displayed visual stimuli may develop high layer neurons with different properties depending on their association with the lower versus the upper portion of the image. Neurons associated with the lower portion of the patterns of performance may learn to recognize error patterns, for example, while neurons associated with the upper portion of the may learn to recognize patterns of performance indicative of normal human functioning, and the like.

Deep convolutional networks (DCNs) are networks of convolutional networks, configured with additional pooling and normalization layers. A DCN may be trained with supervised learning. During training, a DCN may be presented with a pattern of performance for an individual subject without a predetermined condition. The network designer may want the DCN to output a high score for some of the neurons in an output feature vector (e.g., an item analysis), for example the ones corresponding to normal performance in response to displayed visual stimuli. Before training, the output produced by the DCN is likely to be incorrect, and so an error may be calculated between the actual output and the target output. The weights of the DCN may then be adjusted so that the output scores of the DCN are more closely aligned with the target.

After learning, the DCN may be presented with new performance patterns and a forward pass through the network may yield an output that may be considered an inference or a prediction of the DCN for identifying strengths and weaknesses in visual, motor and/or visual-motor functioning of individual subjects in response to displayed visual stimuli.

The parallel filter banks, for example, of a deep convolutional network may be loaded on a CPU 102 or GPU 104 of the computer system 100, optionally based on an ARM instruction set, to achieve high performance and low power consumption. In alternative embodiments, the parallel filter banks may be loaded on the DSP 106 or an ISP 116 of the computer system 100. In addition, the DCN may access other processing blocks that may be present on the computer system 100, such as processing blocks dedicated to the sensor processor 114 and the navigation 120.

Figure 3:
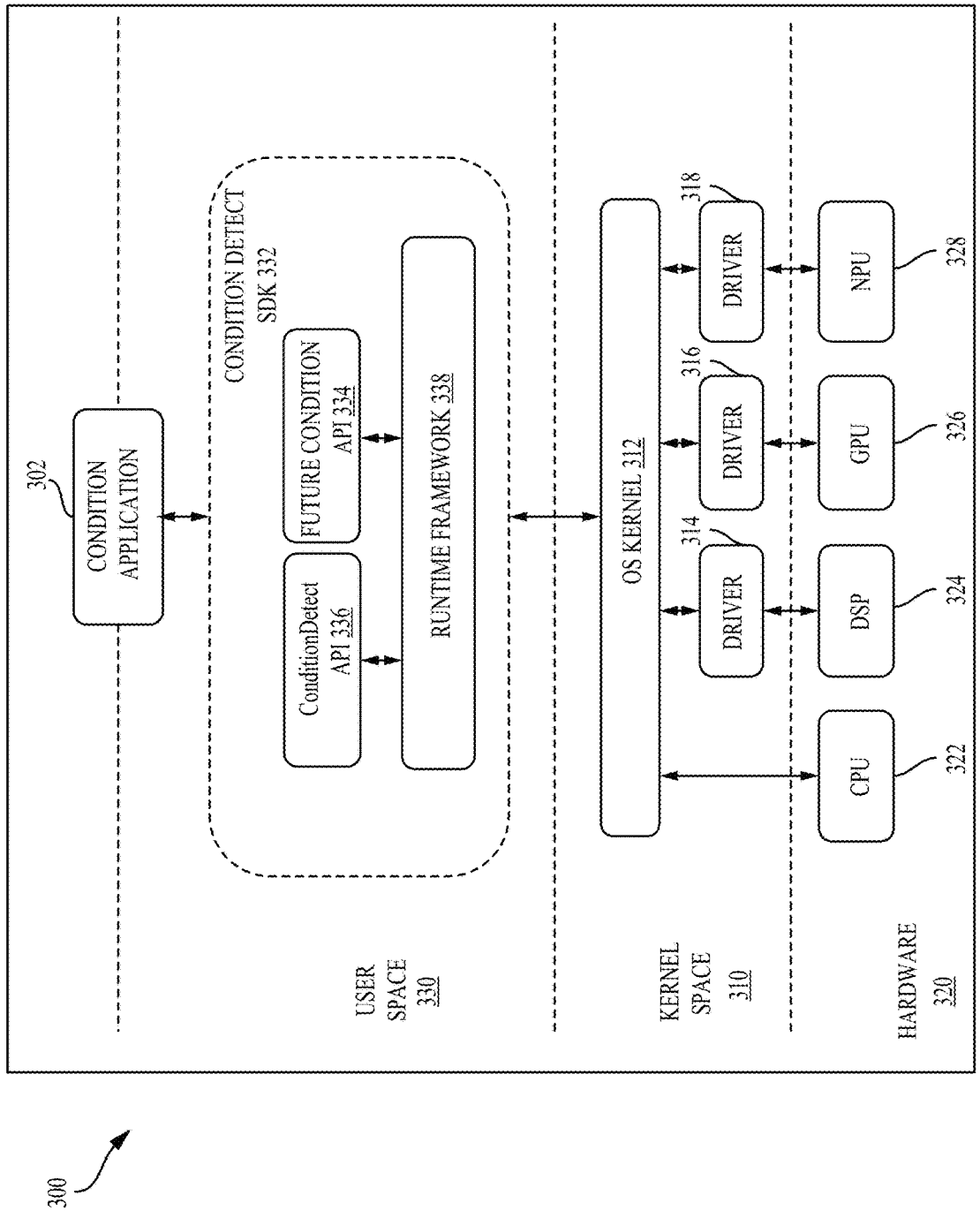
FIG. 3 is a block diagram illustrating an exemplary software architecture that may modularize artificial intelligence (AI) functions in accordance with aspects of the present disclosure.

FIG. 3 is a block diagram illustrating an exemplary software architecture 300 that may modularize functions for profile analysis of an interpretive framework corresponding to at least one condition based at least in part on an item analysis corresponding to a pattern of performance. Using the architecture, a condition application 302 may be designed that may cause various processing blocks of a hardware 320 (for example a CPU 322, a DSP 324, a GPU 326 and/or an NPU 328) to perform supporting computations during run-time operation of the condition application 302 to perform condition detection of an individual subject based on measured visual and visual motor responses to displayed visual stimuli.

The condition application 302 may be configured to call functions defined in a user space 330 that may, for example, provide for the production and display of visual stimuli. The condition application 302 may, for example, configure a display differently depending on whether an individual subject is likely to suffer from a mental condition. The condition application 302 may make a request to compiled program code associated with a library defined in a ConditionDetect application programming interface (API) 336 (or future condition API 334) to provide an estimate of a profile analysis of an interpretive framework corresponding to at least one condition. This request may ultimately rely on the output of a deep neural network configured to provide an assessment of an individual subject based on a score of a condition correlation function corresponding to an item analysis of a pattern of errors determined from the digitally measured visual and visual motor responses of the individual subject, for example.

A run-time engine 338, which may be compiled code of a Runtime Framework, may be further accessible to the condition application 302. The condition application 302 may cause the run-time engine, for example, to request a profile analysis of the interpretive framework corresponding to at least one condition at a particular time interval or triggered by an event detected by the user interface of the condition application 302. When producing a condition correlation function of the item analysis of a pattern of errors determined from the digitally measured visual and visual motor responses of the individual subject, the run-time engine may in turn send a signal to an operating system 310, such as an OS Kernel 312, running on the hardware 320. The operating system 310, in turn, may cause a computation to be performed on the CPU 322, the DSP 324, the GPU 326, the NPU 328, or some combination thereof. The CPU 322 may be accessed directly by the operating system, and other processing blocks may be accessed through a driver, such as a driver 314, 316, and 318 for a DSP 324, for a GPU 326, or for an NPU 328. In the exemplary example, the deep neural network may be configured to run on a combination of processing blocks, such as a CPU 322 and a GPU 326, or may be run on an NPU 328, if present.

Figure 4:
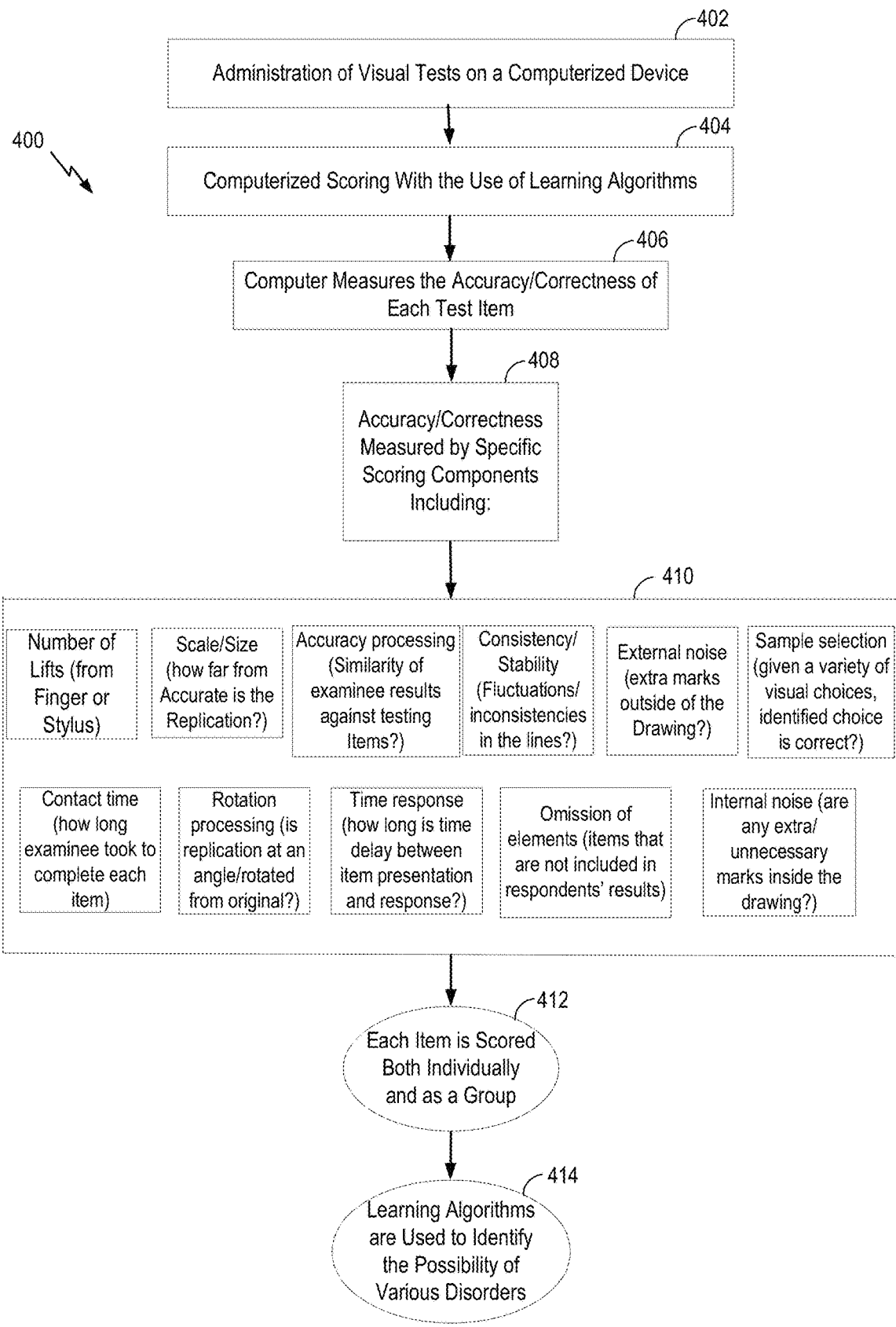
FIG. 4 is flowchart of a visual presentation of the methods used for processing data using learning algorithms that are layered and used in a variety of combinations in accordance with aspects of the present disclosure.

FIG. 4 is flowchart of a visual presentation of a method 400 used for processing data using learning algorithms that are layered and used in a variety of combinations in accordance with aspects of the present disclosure. The method 400 includes digitally measuring responses to visual stimuli on a computerized device through the use of learning algorithms. At block 402, visual test may be administered on a computerized device, such as a mobile device. At block 404, computerized scoring of the visual test is performed using learning algorithms. At block 406, the computerized device measures the accuracy/correctness of each. For example, as shown in FIG. 1, the computer system 100 (e.g., a server device) or the mobile device 140 is used to assess visual motor skills, memory, attention, and other cognitive skills that may be indicative of various conditions of an individual subject.

Referring again to FIG. 4, at block 408, the computerized device determines the accuracy and/or correctness of specific scoring components. As shown in block 410, the computerized device scores components which will include but may not be limited to the following: Number of Lifts (e.g., from finger or stylus), Contact Time (e.g., how long examinee took to complete each item), Accuracy processing (e.g., similarity of examinee results against testing items?), Consistency/Stability (e.g., fluctuations/inconsistencies in the lines?), Internal/External Noise (which are marks made inside or outside of the drawing), Scale/Size (e.g., how far from accurate is the replication?), Sample selection (e.g., given a variety of visual choices, identified choice is correct?), Time response (e.g., how long is time delay between item presentation and response?), Omission of elements (e.g., items that are not included in respondents' results), and Rotation processing (is replication at an angle/rotated from original?). Scoring may also include Matching, Multiple Choice, and Time Delayed Production.

At block 412, each item is scored both individually and as a group. Descriptive information such as the following will also be collected and may inform/impact results: Age, Country, Region/Zip Code, Ethnicity, Handedness, Level of Education, Occupation, Primary/Dominant Language (English Language Learner), Free Lunch, Special Education Services, Medical/Psychiatric/Neurological Diagnoses. At block 414, learning algorithms are used to identify the possibility of various disorders of an individual subject. The measurements are then used to generate correlations to classify and categorize the results into various groups, initially indicating either a possible Disorder/Condition or No Disorder. Additionally, results will be able, with increasing accuracy (learning algorithms), to predict various disorders/conditions as well as recommend additional areas of assessment to further investigate and rule out possible disorders/conditions, for example, as further described in FIG. 5.

Figure 5:
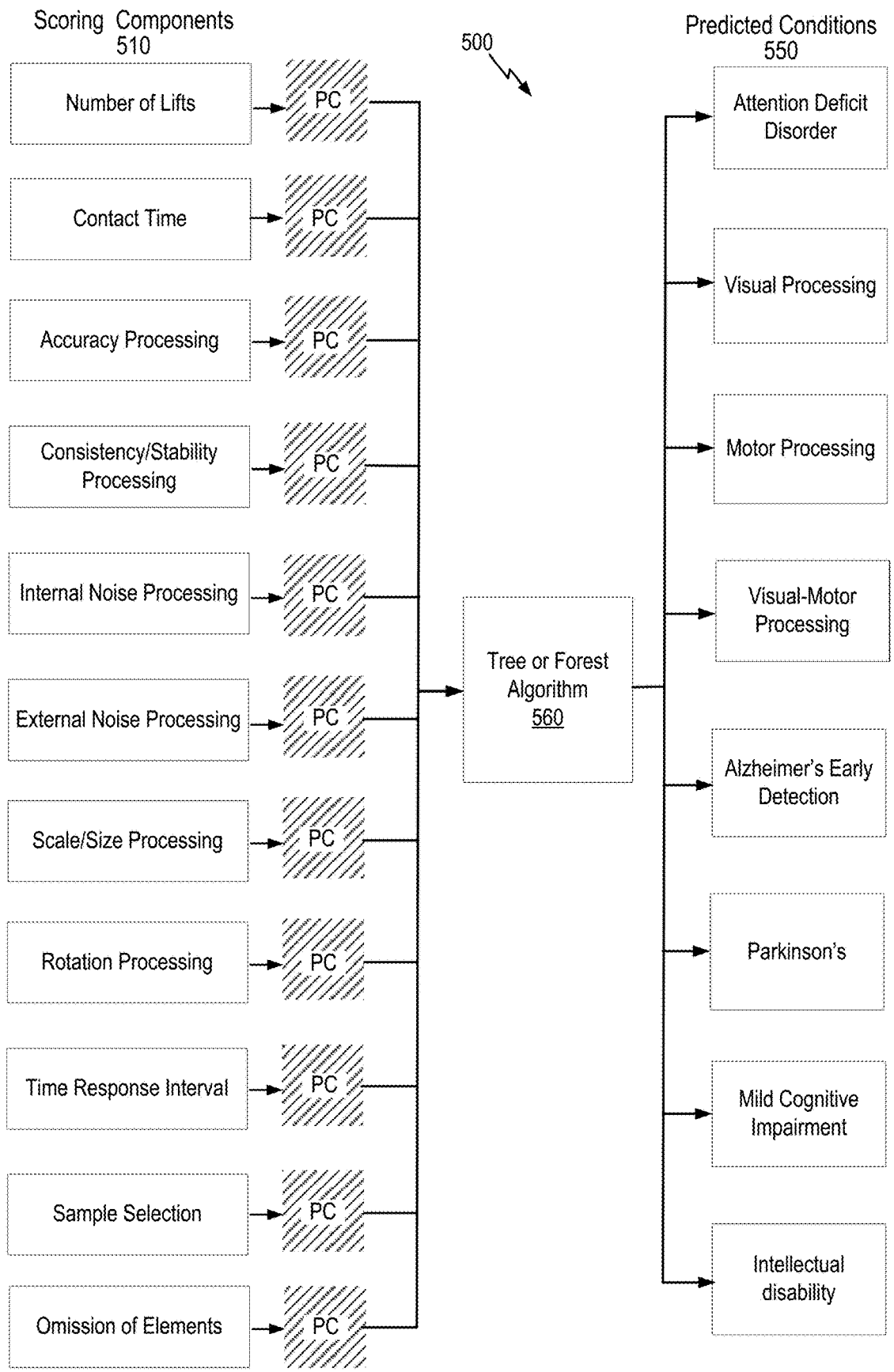
FIG. 5 is a block diagram illustrating system for improving a profile analysis of an interpretive framework based on digital measurement of the production of and responses to visual stimuli according to aspects of the present disclosure.

FIG. 5 is a block diagram illustrating a system 500 for improving a profile analysis of an interpretive framework based on digital measurement of the production of and responses to visual stimuli according to aspects of the present disclosure. Representatively, the system 500 includes two main components that form an automated measurement and classification program. The first component 510 of the system 500 may automate the collection and measurement of multiple key diagnostic features. The second component 550 automates classification into possible conditions/disorders on the basis of the measured features. An individual subject is asked to perform the visual/visual-motor task on a computerized device (e.g., a tablet, a computer, or other mobile device). The system 500 records the drawing and movement patterns and then processes them to produce diagnostic measures. These diagnostic measures are then passed to the second component 550 of the system 500 which uses machine learning techniques to suggest a probable diagnosis/condition and/or suggest additional tests for finding a correct diagnosis.

Figure 6:
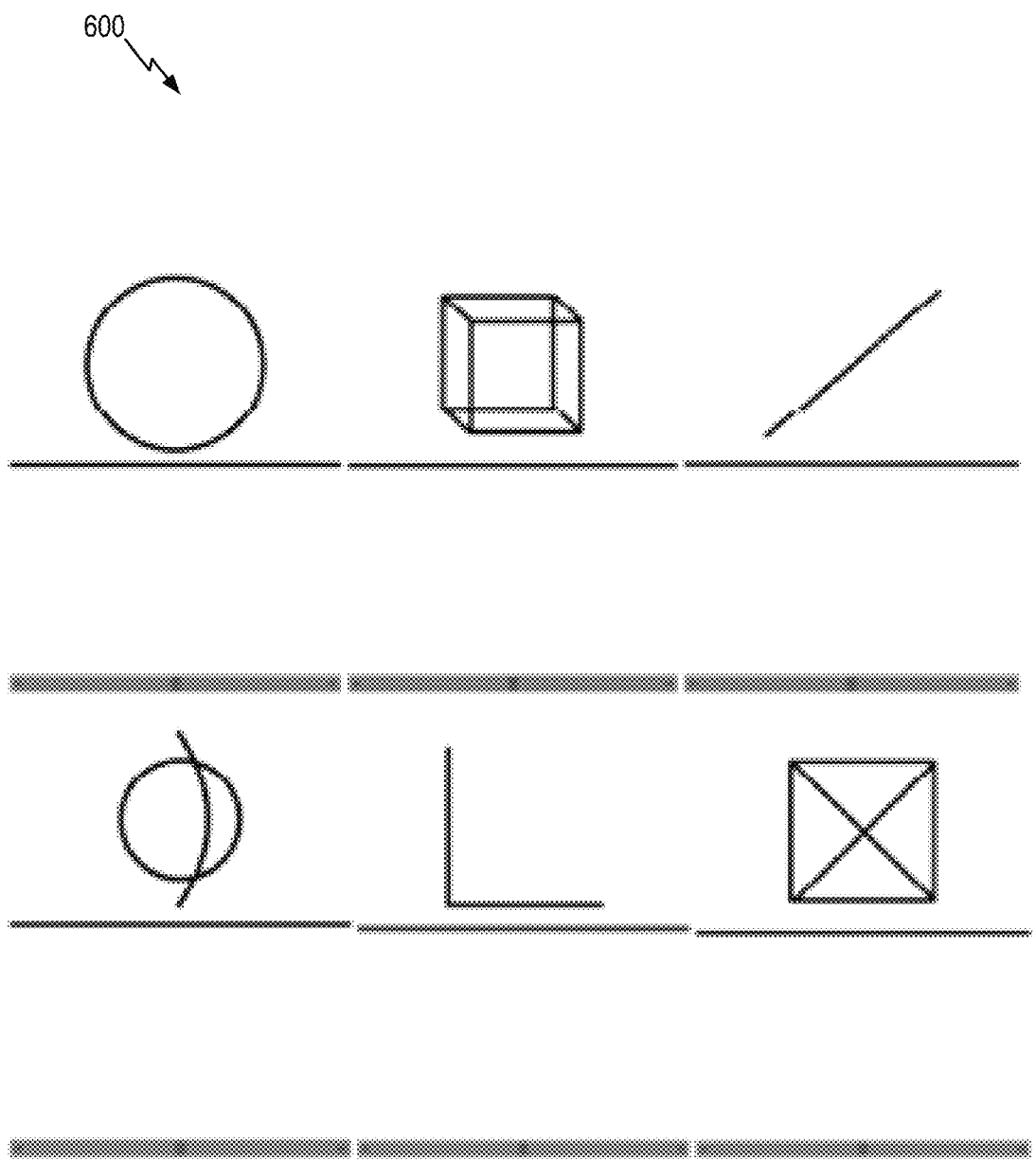
FIG. 6 illustrates visual stimuli in accordance with aspects of the present disclosure.

The first component 510 automates collection of the relevant measures from the diagnostic visual/visual-motor task in response to visual stimuli 600 displayed using a computerized device, for example, as shown in FIG. 6. The measures may be derived from the location and time data for touches on the computerized device directly below the reference image they are asked to view and/or draw in the task. As shown in FIG. 6, an available space for replication is provided between a black line and a grey bar directly below each of the displayed visual stimuli 600. Automating the measurement of these features eliminates bias, manual errors in measurement and provides greater temporal and spatial resolution than manual methods. The features are selected to be diagnostic of different disorders. These features and the methods for determining them are as follows, as computed by the corresponding processing component (PC).

1) Number of Lifts: Simple counter determined by the number of touch events on the computerized device which have a greater temporal length than a minimum constant x.

$$\text{Lifts} = \{\text{touch} | (\text{touch}_{end} - \text{touch}_{start}) > x\} \quad (1)$$

2) Contact Time: Statistical measures of contact time for all touch events including but not limited to mean contact time and standard deviation of contact times, where x is the contact time.

$$x = (touch_{end} - touch_{start}), \; Mean_{contact\;time} = \sum_{n=1}^{n} x_i / n \quad (2)$$

$$SD_{contact\;time} = \sqrt{\frac{1}{N} \sum_{i=1}^{N} (x_i - \bar{x})^2} \quad (3)$$

3) Speed and Timing: Statistical measures of speed for all touch events including but not limited to mean speed and standard deviation of speed, where speed s is approximated by the distance between start and end points of touch events and the duration of contact.

$$s = \sqrt{(x_2-x_1)^2 + (y_2-y_1)^2}/CT, \text{Mean}(S), \text{Standard Deviation}(S) \quad (4)$$

4) Response Interval Timing (for memory test): Statistical measures of response interval timing from the memory test portion of the task. Including but not limited to: mean and standard deviation of the time between successive responses, here labeled RI.

$$Mean_{RI} = \sum_{i=1}^{n} RI_i/n, \; SD_{RI} = \sqrt{\frac{1}{N} \sum_{i=1}^{N} (RI_i - \overline{RI})^2} \quad (5)$$

5) Acceleration: Statistical measures of acceleration for all touch events including but not limited to mean acceleration and standard deviation of acceleration, where acceleration a is approximated by the average acceleration over some period of time x.

$$\overline{a_x} = \frac{\Delta v_x}{\Delta t_x}, \; Mean_a = \sum_{i=1}^{n} a_i/n, \; SD_a = \sqrt{\frac{1}{N} \sum_{i=1}^{N} (a_i - \bar{a})^2} \quad (6)$$

6) Accuracy: Measure of the accuracy of the drawing to the reference image determined using either or both of keypoint matching or texture histogram comparison between the two images.

7) Line Consistency/Stability: Measures of the overall consistency of lines in the image, these include but are not limited to the consistency of each line, approximated by the variance of accelerations within that line. The overall line consistency in an image is approximated by the average of line variances.

$$LC = \sqrt{\frac{1}{N}\sum_{i=1}^{N}(a_i - \bar{a})^2} \text{ where } \{a \setminus a \varepsilon \, line_i\} \quad (7)$$

8) Scale/Size: A simple pixel measure of the height and width of the drawing from its furthest points in the X and Y planes. Absolute size of drawing may be divided by absolute size of original image to determine a scaling factor.

$$Size_X=(Max_X-Min_X), Size_Y=(Max_Y-Min_Y) \quad (8)$$

$$Scale_X=(sizeX_{draw}/sizeX_{original}), Scale_Y=(sizeY_{draw}/sizeY_{original}) \quad (9)$$

9) Rotation: A measure of the rotation of the image is derived algorithmically using keypoint extraction of original and drawn image performed for trait 6. Rotational transformations are applied to the keypoints of the drawn image until the difference between the relative angles of the keypoints is smallest. The determined angle of rotation is then used as the measure.

10) Internal Noise/External Noise: Measures of the noise (stray lines and marks) inside of or outside of the main drawing area, defined here as the rectangular area within which 90% of all the pixels fall. This includes but is not limited to a count measure of all marks that are non-contiguous to other marks and are less than x % of the length of the longest contiguous mark in the drawing. These small marks are considered "noise". Internal noise if they fall within the main drawing area and external noise if they fall outside of it.

$$Noise = \left\{Mark \setminus length\,(Mark) < \left(\frac{x}{100} * length(LongestMark)\right)\right\} \quad (10)$$

The second component 550 of the system 500 automates the classification of individuals into possible conditions/diagnoses on the basis of the previously listed features. The system uses machine learning techniques (e.g., tree/forest algorithm 560), described below, to increase the accuracy of a possible classification. There are two relevant pieces of the classification system: the algorithm for classification and the training set. The training set is a reference set of individuals who are known to truly belong to one of the categories along with their performance on each of the measures listed above. The algorithm for classification then learns an optimal way of using these measures (features) to classify the known individuals into their respective categories. Provided that the categories are possible to separate on the basis of these features, machine learning algorithms are proven to find a method of correctly categorizing individuals.

Although the listed features may be used to differentiate between possible disorders, other features may be used as necessary to differentiate between possible disorders. In aspects of the present disclosure, a representative sample of individuals with known psychological/medical/neurological disorders or lack thereof will be collected as a training set. The learning algorithm will be trained on this data and produce a method of correctly classifying individuals with unknown status into a category based on the features from the test. This method will then be used to suggest a probable diagnosis for individuals given the visual/visual-motor test, or if there is insufficient data to allow a categorization, additional tests are suggested.

According to aspects of the present disclosure, example types of categories for classification include, but are not limited to: (1) no identifiable issues; (2) attention deficit disorder; (3) visual processing; (4) motor processing; (5) visual-motor processing; (6) memory; (7) Alzheimer's; (8) Parkinson's; (9) mild cognitive delay; and/or (10) intellectual disability. In this aspect of the present disclosure, the classification system is a machine learning, multiclass classification system using classification trees. For example, the machine learning, multiclass classification system may use classification trees trained with a predetermined algorithm (e.g., the C4.5 Algorithm).

In one aspect of the present disclosure, the system 500 uses an algorithm (e.g., the C4.5 algorithm) to create a classification tree to improve classification of individual subjects into a class based on their performance in a visual-motor drawing task. For example, in C4.5 algorithm, the decision tree is built from a training set (S=s1, s2, sn) of classified data, where each training instance s consists of the vector of n features from the drawing task (P=p1, p2, ..., pn). In this example, normalized information gain is used to find the feature p that most effectively partitions the training samples into their different classes. This process is repeated for the newly created subsets until all instances in each subset are of the same class.

For example, the C4.5 Algorithm may be used to form a classification tree using the following process.

1. Check for possible base cases;
   a. if all samples are of the same class then simply create a leaf node for that class;
   b. if no features provide information gain then create a parent decision node using the expected value for each class;
   c. if a new class is encountered a parent decision node is created using the expected value of the new class;
2. iterate through all attributes a and find the normalized information gain for partitioning on each attribute;
3. take the attribute a' with the highest information gain;
4. make a new decision node that partitions based on a'; and
5. repeat on all sub-lists created from partitioning on a' and set those nodes as children of the current decision node.

Although classification tree formation is described with reference to the C4.5 Algorithm, aspects of the present disclosure are not so limited. For example, an ensemble method, decision forests, may be used where a multitude of different decision trees are created at training time and new samples are partitioned based on the mode category output of this set of n decision trees. Single decision trees are not guaranteed to converge on the globally optimum function so an ensemble can improve performance for diagnosis classification.

Figure 7:
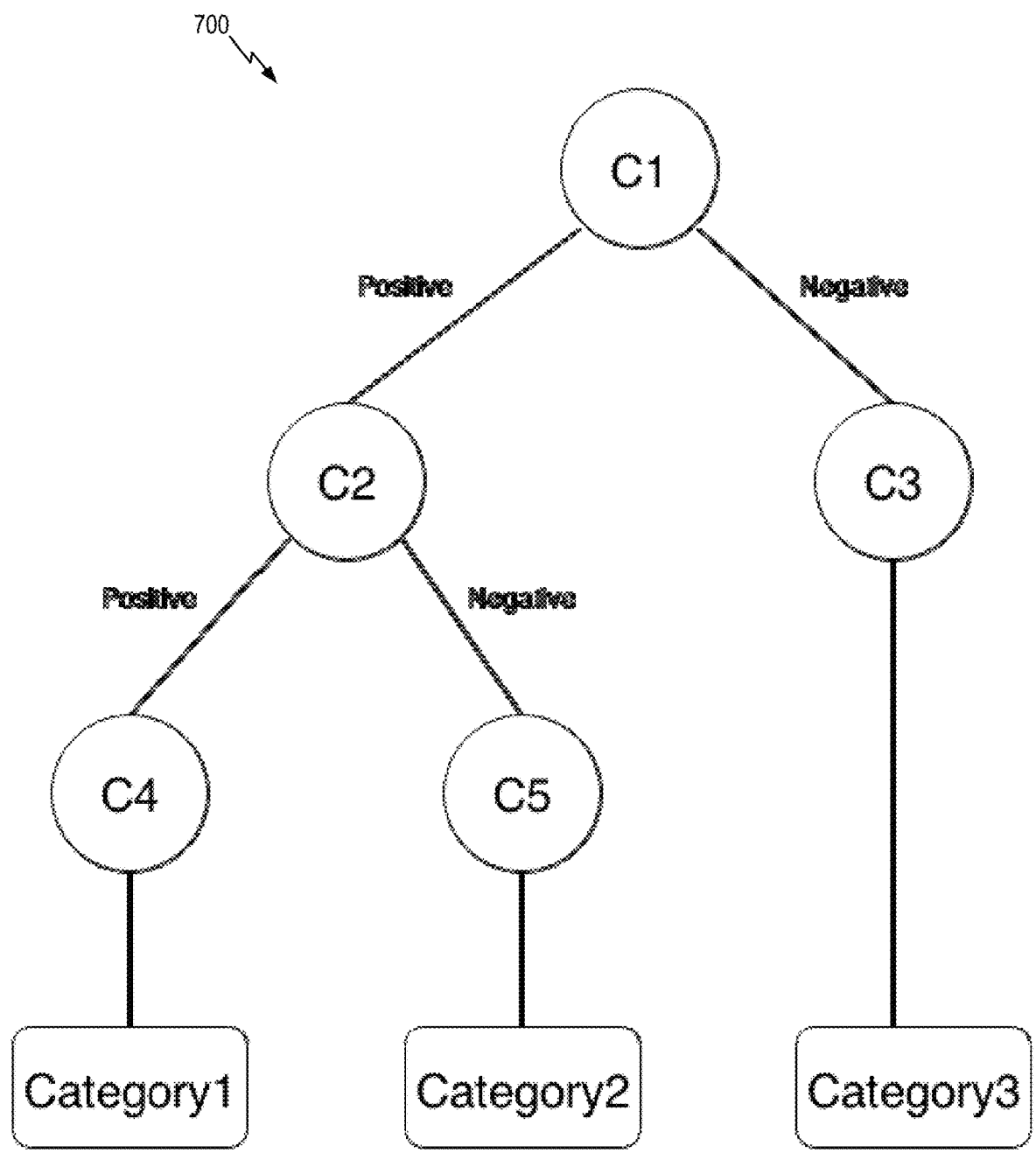
FIG. 7 illustrate a multiclass classification tree with binary classifiers and hierarchical components for three target categories according to aspects of the present disclosure.

FIG. 7 illustrate a multiclass classification tree 700 with binary classifiers and hierarchical components for three target categories according to aspects of the present disclosure. The described system will provide a multi-class classification into one of the n possible target categories. The categories may include both hierarchical components (e.g., motor-processing disorders then subdivided into specific motor-processing disorders) and non-hierarchical components (e.g., attention deficit hyperactivity disorder with no subcategories or super categories). The hierarchical categories may also be used to prompt for additional tests. As in the case where the decision tree classifies an individual into motor-processing disorders but lacks enough information to confidently classify them into a specific disorder. The system will then output the general diagnosis and suggest a further test for diagnosing different motor disorders.

The system will implement current state of the art algorithms for multi-class classification, such as using decision trees or forests trained using a predetermined training algorithm (e.g., the C4.5 algorithm), support vector machines or a boosted combination of both to provide optimal performance. A predetermined method (e.g., a one vs all, all vs all, or error correcting output codes) may be used to map binary classifiers to the multiclass problem or to improve performance. The system is tuned to give optimal results for imbalanced multi-class problems where uneven portions of the population may fall in any given category. The system outputs a classification of the feature vector (e.g., what disorder (if any) is potentially present based on the responses).

For example, using the C4.5 algorithm, the multiclass classification tree 700 is built from a training set (S=s1, s2, sn) of classified data where each training instance s consists of a vector of n psychologically relevant features (P=p1, p2 . . . pn). Normalized information gain is used to find the feature p that most effectively partitions the training samples into their different classes:

$$D_{KL}(P\|Q) = \sum_i P(i)\ln\frac{P(i)}{Q(i)}.$$

Information Gain for Discrete Variable; and $$D_{KL}(P\|Q) = \int_{-\infty}^{\infty} p(x)\ln\frac{p(x)}{q(x)}dx,$$

Information Gain for Continuous Variable.

The most partitioning feature becomes the first classifier leaf in the decision tree. The algorithm is then applied iteratively for all n features in the vector P to train a tree that can partition new samples into a category based on their feature vector S. Optionally an ensemble method, decision forests, may be used where a multitude of different decision trees are created at training time and new samples are partitioned based on the mode category output of this set of n decision trees. Single decision trees are not guaranteed to converge on the globally optimum function so an ensemble can improve performance.

In some aspects, the present disclosure uses support vector machines for classification. Support vector machines are a non-probabilistic binary linear classifier. A support vector machine will train a classification from a training set S, where S is an instance with a vector P of features and a known classification. The support vector machine finds the linear division that separates instances from S into two categories with the largest possible space between the linear division and all instances s from the training set represented by points in an N-dimensional feature space where N=length (P). The maximum-margin hyperplane. Kernel methods may also be used which allow non-linear divisions by implicitly mapping the division into a higher dimensional feature space.

Binary methods such as support vector machines require expansion to work as multi-class classifiers so one or a combination of the following standard methods for expanding binary classifiers to multiclass problems will be used, whichever leads to optimal performance:

One vs All: where a binary classifier is trained for each possible division between a category c and all other categories in C and the classified category is decided by the classifier producing the highest confidence score;

One vs One: where a binary classifier is trained for each possible combination of a category c to another category c, resulting in N (N−1)/2 total classifiers where N is the number of categories in C. The classified category is decided by the category c with the largest number of classifiers positively identifying it.

Error Correcting Output Codes: a binary classifier is trained for each possible combination of a category c to another category c and a codeword of length N where N is the number of classifiers trained is specified for each category. Each bit of the codeword encodes the output of a given classifier. The classified category is determined by generating a codeword for each new instance and classifying it as the category whose codeword has the shortest bitwise distance from the generated codeword.

Figure 8:
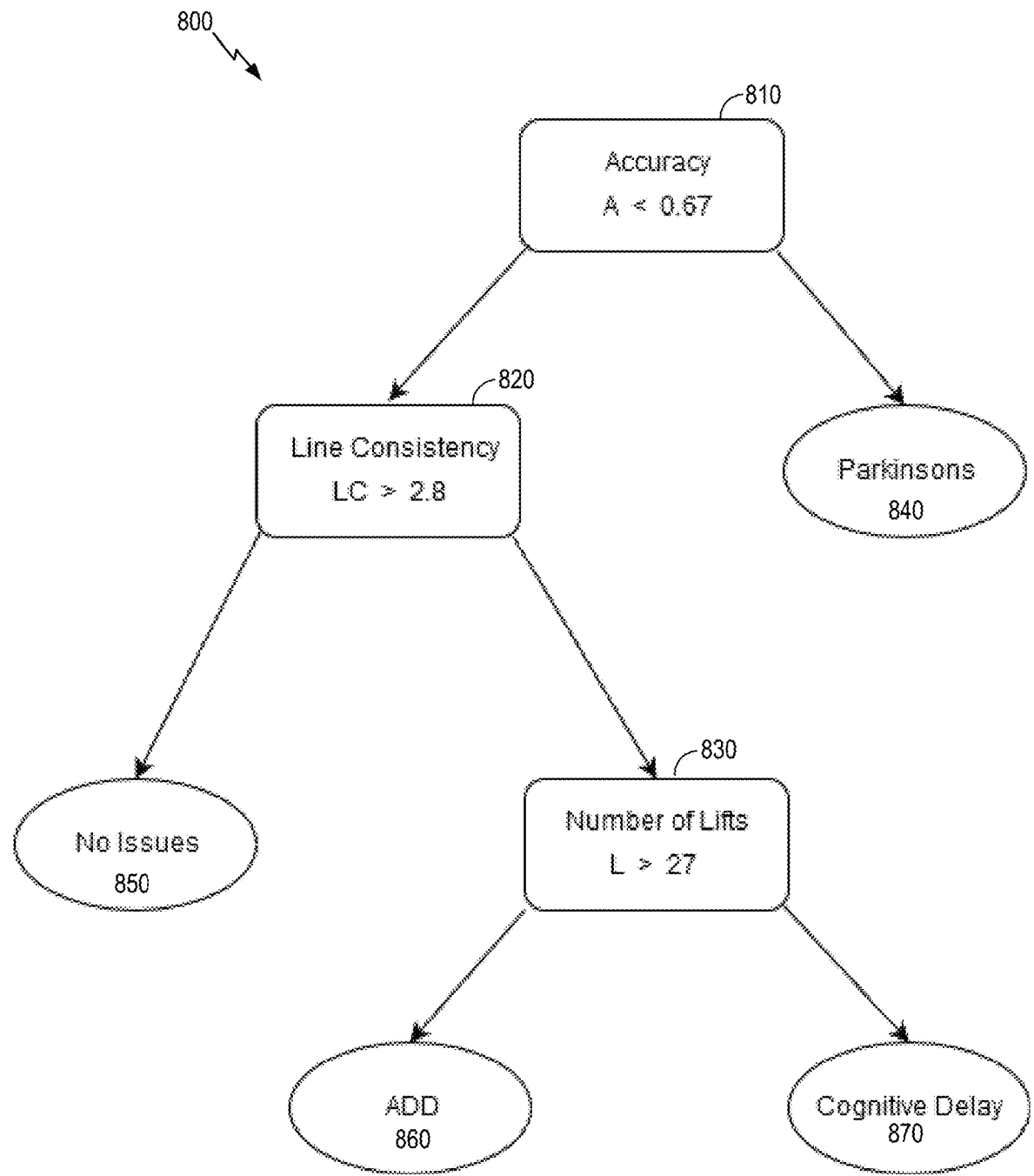
FIG. 8 illustrates a visual-motor task classification tree according to an aspect of the present disclosure.

FIG. 8 illustrates a visual-motor task classification tree according to an aspect of the present disclosure. A classification tree is a type of decision tree where the terminal nodes of the tree (leaf nodes) are a categorical variable. In this case the categorical outputs are one of the conditions/psychological categories for classification (e.g., attention deficit disorder, Parkinson's, no identifiable issues, etc.) The training features are used to partition the data into branches that separate individuals into the correct diagnosis classes.

Representatively, the classification tree 800 illustrates a categorical variable for accuracy 810, categorical variable for line consistency 820, and categorical variable for number of lifts 830. In this example, an accuracy (A) greater than a predetermined value (i.e., A>0.67) may be indicative of a Parkinson's diagnosis 840. Otherwise, the branch to the categorical variable for line consistency 820 is taken. In this arrangement of the classification tree 800, a line consistency (LC) greater than a predetermine value (i.e., LC>2.8) may be indicative of a no issues diagnosis 850. Nevertheless, a number of lifts (L) greater than a predetermine value (i.e., L>27) may be indicative of an attention deficit disorder (ADD) diagnosis 860 when the line consistency is less than a predetermine value (i.e., L<2.8). Otherwise, a number of lifts is less than the predetermined value (i.e., L<27) may be indicative of a cognitive delay diagnosis 870.

Figure 9:
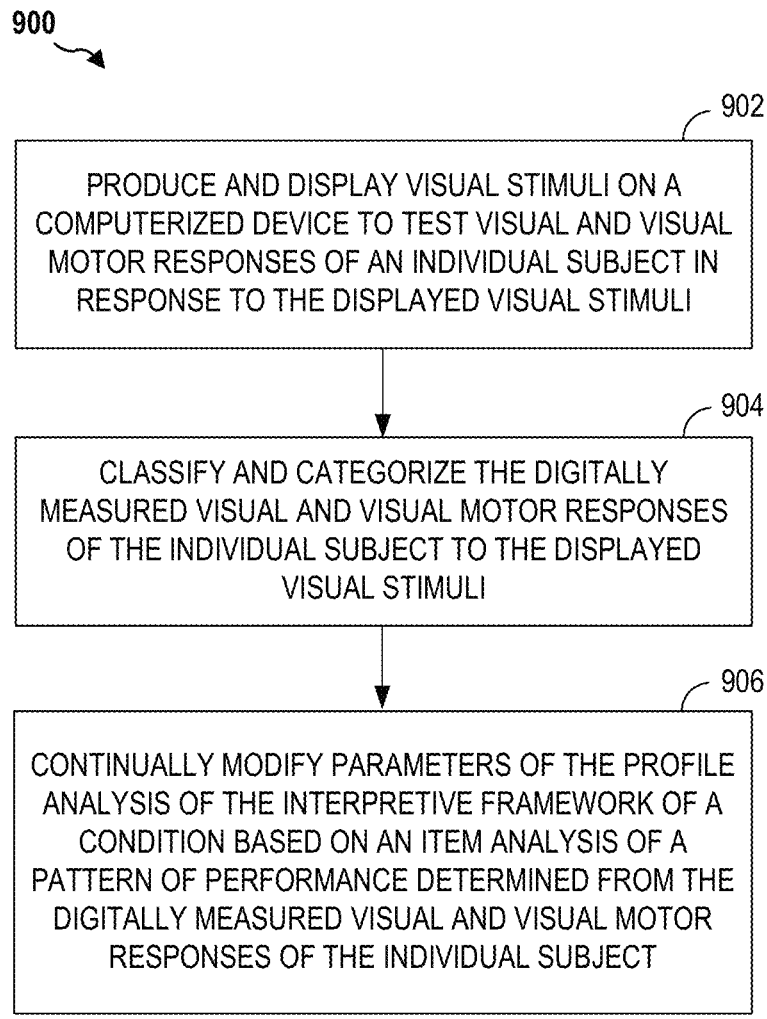
FIG. 9 illustrates a method for improving a profile analysis of an interpretive framework based on digital measurement of the production of and responses to visual stimuli in accordance with aspects of the present disclosure.

FIG. 9 illustrates a method 900 for improving a profile analysis of an interpretive framework based on digital measurement of the production of and responses to visual stimuli in accordance with aspects of the present disclosure. In block 902, visual stimuli is produced and displayed on a computerized device to test visual and visual motor responses of an individual subject in response to the displayed visual stimuli. For example, the visual stimuli 600 shown in FIG. 6 may be displayed to an individual subject using the display 130 of the computer system 100 or the mobile device 140. In addition, visual and visual motor responses of the individual subject to the displayed visual stimuli are digitally measured. In block 904, the digitally measured visual and visual motor responses of the at least one individual subject to the displayed visual stimuli are classified and categorized. For example, as shown in FIG. 7, the digitally measured visual and visual motor responses may be classified and categorized with binary classifiers (e.g., C1, C2, C3, C4, and C5) into one of the three target categories (e.g., Category1, Category2, and Category3).

Referring again to FIG. 9, in block 906, parameters of the profile analysis of the interpretive framework of a condition are continually modified based on an item analysis of a pattern of performance determined from the digitally measured visual and visual motor responses of the individual subject. For example, as shown in FIG. 8, baseline values for the categorical variable for accuracy 810, the categorical variable for line consistency 820, and the categorical variable for number of lifts 830 may be determined based on the item analysis of the performance of an individual subject based on of the digitally measured visual and visual motor responses when the individual subject does not suffer from the conditions. The categorical values may then be adjusted based on the digitally measured visual and visual motor responses of an individual subject that suffers from one of the conditions. In this way, the categorical values may adapt to the digitally measured performance data over time such that the system may be considered to include condition correlation function learning.

Figure 10:
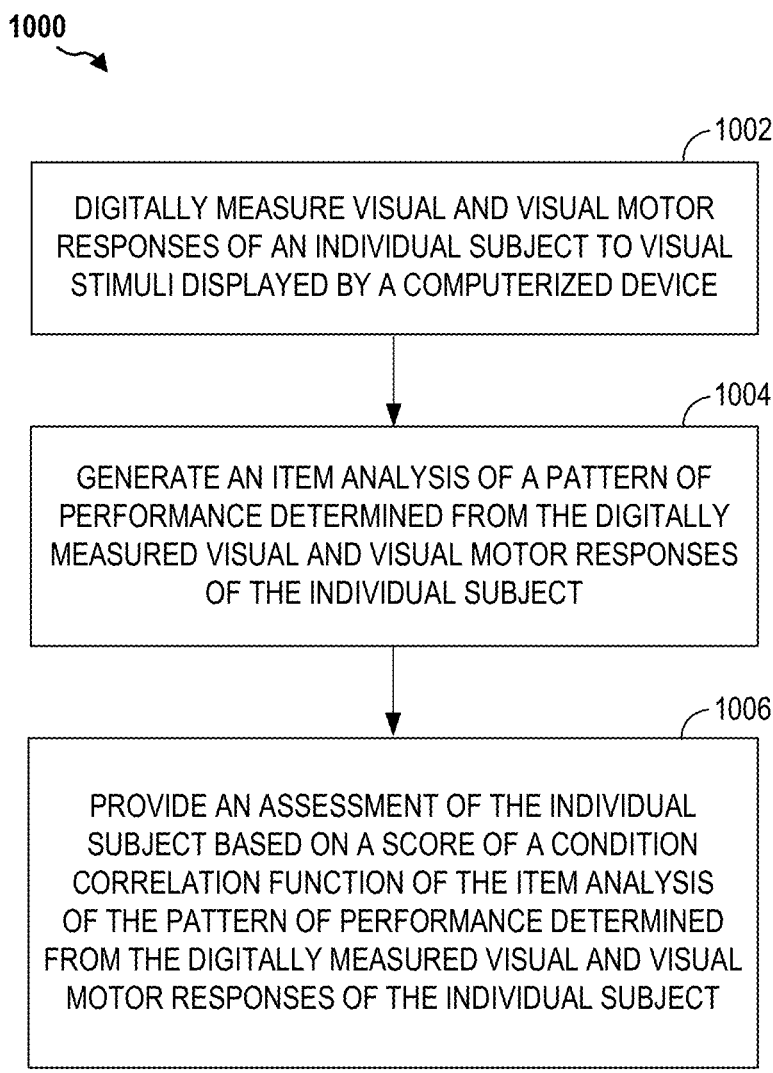
FIG. 10 illustrates a method for a diagnostic profile analysis of an individual subject according to an interpretive framework in aspects of the present disclosure.

FIG. 10 illustrates a method 1000 for a diagnostic profile analysis of an individual subject according to an interpretive framework in aspects of the present disclosure. In block 1002, visual and visual motor responses of an individual subject to visual stimuli produced and displayed on a computerized device are digitally measured. For example, the visual stimuli 600 shown in FIG. 6 may be displayed to an individual subject using the display 130 of the computer system 100 or the mobile device 140. The visual and visual motor responses of the individual to the displayed visual stimuli are digitally measured to enable mental health disorder testing of the individual subject. In block 1004, an item analysis of to a pattern of performance determined from the digitally measured visual and visual motor responses of the individual subject is generated. For example, as shown in FIG. 5, the item analysis may include the various scoring components collected by the first component 510 of the relevant measures from the diagnostic visual/visual-motor task in response to visual stimuli 600 shown in FIG. 6.

Referring again to FIG. 10, in block 1006, an assessment of the individual subject is provided based on a score of a condition correlation function of the item analysis of the pattern of performance determined from the digitally measured visual and visual motor responses of the individual subject. For example, as shown in FIG. 5, the tree/forest algorithm 560 computes a condition correlation function based on the item analysis of the performance of the individual subject based on the digitally measured visual and visual motor responses. The second component 550 of the system 500 automates the classification of individuals into possible conditions/diagnoses on the basis of the previous item analysis. The system uses machine learning techniques (e.g., tree/forest algorithm 560), described above, to increase the accuracy of a possible classification. In this way, the predicted conditions may adapt to the digitally measured performance data over time such that the system may be considered to include predicted condition learning.

Aspects of the present disclosure include a psychometric tool to measure psychological/neurological/medical conditions by administering and scoring responses to visually presented tests on computerized devices. The scoring allows the computerized device to generate an item analysis that describes patterns of errors made by an individual subject. This error analysis, combined with appropriate factor analysis of the items provides an interpretive framework for profile analysis that makes interpretation far more accurate and diagnostically meaningful than the single standard scores that result from existing tests of this type. Additionally the tool, through learning algorithm analyses of the response patterns, will gain increasing accuracy to provide predictive information on possible conditions (showing similar patterns), and/or suggesting other areas of investigation to rule out possible conditions suggested by the scores. In this way, the psychometric tool may adapt to the data over time and the tool may be considered to include condition learning.

The various operations of methods described above may be performed by any suitable means capable of performing the corresponding functions. The means may include various hardware and/or software component(s) and/or module(s), including, but not limited to, a circuit, an application specific integrated circuit (ASIC), or processor. Generally, where there are operations illustrated in the figures, those operations may have corresponding counterpart means-plus-function components with similar numbering.

As used herein, the term "determining" encompasses a wide variety of actions. For example, "determining" may include calculating, computing, processing, deriving, investigating, looking up (e.g., looking up in a table, a database or another data structure), ascertaining and the like. Additionally, "determining" may include receiving (e.g., receiving information), accessing (e.g., accessing data in a memory) and the like. Furthermore, "determining" may include resolving, selecting, choosing, establishing and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logical blocks, modules and circuits described in connection with the present disclosure may be implemented or performed with a general-purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general-purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the present disclosure may be embodied directly in hardware, in a software module executed by a processor, or in a combination of the two. A software module may reside in any form of storage medium that is known in the art. Some examples of storage media that may be used include random access memory (RAM), read only memory (ROM), flash memory, erasable programmable read-only memory (EPROM), electrically erasable programmable read-only memory (EEPROM), registers, a hard disk, a removable disk, a CD-ROM and so forth. A software module may comprise a single instruction, or many instructions, and may be distributed over several different code segments, among different programs, and across multiple storage media. A storage medium may be coupled to a processor such that the processor can read information from, and write information to, the storage medium. In the alternative, the storage medium may be integral to the processor.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The functions described may be implemented in hardware, software, firmware, or any combination thereof. If implemented in hardware, an example hardware configuration may comprise a processing system in a device. The processing system may be implemented with a bus architecture. The bus may include any number of interconnecting buses and bridges depending on the specific application of the processing system and the overall design constraints. The bus may link together various circuits including a processor, machine-readable media, and a bus interface. The bus interface may be used to connect a network adapter, among other things, to the processing system via the bus. The network adapter may be used to implement signal processing functions. For certain aspects, a user interface (e.g., keypad, display, mouse, joystick, etc.) may also be connected to the bus. The bus may also link various other circuits such as timing sources, peripherals, voltage regulators, power management circuits, and the like, which are well known in the art, and therefore, will not be described any further.

The processor may be responsible for managing the bus and general processing, including the execution of software stored on the machine-readable media. The processor may be implemented with one or more general-purpose and/or special-purpose processors. Examples include microprocessors, microcontrollers, DSP processors, and other circuitry that can execute software. Software shall be construed broadly to mean instructions, data, or any combination thereof, whether referred to as software, firmware, middleware, microcode, hardware description language, or otherwise. Machine-readable media may include, by way of example, random access memory (RAM), flash memory, read only memory (ROM), programmable read-only memory (PROM), erasable programmable read-only memory (EPROM), electrically erasable programmable Read-only memory (EEPROM), registers, magnetic disks, optical disks, hard drives, or any other suitable storage medium, or any combination thereof. The machine-readable media may be embodied in a computer-program product. The computer-program product may comprise packaging materials.

In a hardware implementation, the machine-readable media may be part of the processing system separate from the processor. However, as those skilled in the art will readily appreciate, the machine-readable media, or any portion thereof, may be external to the processing system. By way of example, the machine-readable media may include a transmission line, a carrier wave modulated by data, and/or a computer product separate from the device, all which may be accessed by the processor through the bus interface. Alternatively, or in addition, the machine-readable media, or any portion thereof, may be integrated into the processor, such as the case may be with cache and/or general register files. Although the various components discussed may be described as having a specific location, such as a local component, they may also be configured in various ways, such as certain components being configured as part of a distributed computing system.

The processing system may be configured as a general-purpose processing system with one or more microprocessors providing the processor functionality and external memory providing at least a portion of the machine-readable media, all linked together with other supporting circuitry through an external bus architecture. Alternatively, the processing system may comprise one or more neuromorphic processors for implementing the neuron models and models of neural systems described herein. As another alternative, the processing system may be implemented with an application specific integrated circuit (ASIC) with the processor, the bus interface, the user interface, supporting circuitry, and at least a portion of the machine-readable media integrated into a single chip, or with one or more field programmable gate arrays (FPGAs), programmable logic devices (PLDs), controllers, state machines, gated logic, discrete hardware components, or any other suitable circuitry, or any combination of circuits that can perform the various functionality described throughout this disclosure. Those skilled in the art will recognize how best to implement the described functionality for the processing system depending on the particular application and the overall design constraints imposed on the overall system.

The machine-readable media may comprise a number of software modules. The software modules include instructions that, when executed by the processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During execution of the software module, the processor may load some of the instructions into cache to increase access speed. One or more cache lines may then be loaded into a general register file for execution by the processor. When referring to the functionality of a software module below, it will be understood that such functionality is implemented by the processor when executing instructions from that software module. Furthermore, it should be appreciated that aspects of the present disclosure result in improvements to the functioning of the processor, computer, machine, or other system implementing such aspects.

If implemented in software, the functions may be stored or transmitted over as one or more instructions or code on a computer-readable medium. Computer-readable media include both computer storage media and communication media including any medium that facilitates transfer of a computer program from one place to another. A storage medium may be any available medium that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Additionally, any connection is properly termed a computer-readable medium. For example, if the software is transmitted from a website, server, or other remote source using a coaxial cable, fiber optic cable, twisted pair, digital subscriber line (DSL), or wireless technologies such as infrared (IR), radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk, and Blu-ray® disc where disks usually reproduce data magnetically, while discs reproduce data optically with lasers. Thus, in some aspects computer-readable media may comprise non-transitory computer-readable media (e.g., tangible media). In addition, for other aspects computer-readable media may comprise transitory computer-readable media (e.g., a signal). Combinations of the above should also be included within the scope of computer-readable media.

Thus, certain aspects may comprise a computer program product for performing the operations presented herein. For example, such a computer program product may comprise a computer-readable medium having instructions stored (and/or encoded) thereon, the instructions being executable by one or more processors to perform the operations described herein. For certain aspects, the computer program product may include packaging material.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

What is claimed is:

1. A method for improving a profile analysis of an interpretive framework stored in a memory, comprising:
   producing and displaying visual stimuli on a display of a computerized device of a visual-motor drawing task;
   digitally measuring visual and visual motor responses of an individual subject in response to drawings of the displayed visual stimuli drawn directly on the display of the computerized device by the individual subject to replicate the displayed visual stimuli in a corresponding available space of the display, directly below the displayed visual stimuli to complete the visual-motor drawing task;
   deriving a set of features from the visual and visual motor responses that includes:
   measuring a number of lifts, a contact time, a speed and timing, and an acceleration performed by the individual subject to replicate the displayed visual stimuli and complete the visual-motor drawing task;
   calculating accelerations as an average change in length of drawn lines over time of a replication;
   calculating a line consistency according to a variance of the accelerations within the drawn lines of the replication;
   calculating a scale of the replication relative to the displayed visual stimuli;
   calculating a rotation according to a minimum value of a rotational transformation of keypoints between the replication and the displayed visual stimuli;
   calculating non-contiguous marks within and outside a rectangular area occupied by ninety percent of the pixels of the replication and less than a predetermined percentage of a length of a longest contiguous mark;
   training a machine learning model to classify and categorize the digitally measured visual and visual motor responses using the derived set of features;
   identifying parameters of the profile analysis of the interpretive framework corresponding to the parameters of the trained machine learning model;
   classifying and categorizing, using the trained machine learning model, the digitally measured visual and visual motor responses of the individual subject to the displayed visual stimuli according to the derived set of features;
   recognizing a pattern of performance errors associated with the individual subject in response to the displayed visual stimuli corresponding to at least one condition based on the classification and categorization, wherein the at least one condition includes a psychological disorder or a neurological disorder; and
   continually modifying parameters of the profile analysis of the interpretive framework corresponding to the parameters of the trained machine learning model for the at least one condition based at least in part on the pattern of performance errors.

2. The method of claim 1, in which said continually modifying the parameters comprises establishing a baseline for the parameters of the profile analysis of the interpretive framework corresponding to the at least one condition based at least in part on an analysis of the pattern of performance errors determined during the classifying and categorizing of the digitally measured visual and visual motor responses of the individual subject when the individual subject does not suffer from the at least one condition.

3. The method of claim 1, in which said continually modifying comprises adjusting the parameters of the profile analysis of the interpretive framework corresponding to the at least one condition based at least in part on an analysis of the pattern of performance errors determined during the classifying and categorizing of the digitally measured visual and visual motor responses of the individual subject when the individual subject suffers from the at least one condition.

4. The method of claim 1, in which said classifying and categorizing the digitally measured visual and visual motor responses further comprises identifying strengths and weaknesses in visual, motor or visual-motor functioning of the individual subject in response to the visual stimuli displayed using the computerized device.

5. The method of claim 1, in which said continually modifying comprises:
   adjusting the parameters of the profile analysis of the interpretive framework corresponding to the at least one condition based at least in part on an analysis of the pattern of performance errors determined during the classifying and categorizing of the digitally measured visual and visual motor responses of the individual subject; and
   providing an assessment of the individual subject based at least in part on a score of a condition correlation function corresponding to the analysis of the pattern of performance errors determined from the digitally measured visual and visual motor responses of the individual subject.

6. The method of claim 5, further comprising predicting a potential condition of the individual subject when the score of the condition correlation function corresponding to the analysis of the pattern of performance errors determined from the digitally measured visual and visual motor responses of the individual subject is within a predetermined range.

7. The method of claim 5, further comprising eliminating at least one potential condition based at least in part on the score of the condition correlation function corresponding to the analysis of the pattern of performance errors determined from the digitally measured visual and visual motor responses of the individual subject.

8. The method of claim 1, in which said continually modifying the parameters further comprising updating a condition correlation function corresponding to the at least one condition according to the classifying and categorizing of the digitally measured visual and visual motor responses of the individual subject when the individual subject suffers from the at least one condition.

9. An apparatus configured to improve a profile analysis of an interpretive framework, the apparatus comprising:
   a display;
   a memory configured to store the interpretive framework; and
   at least one processor coupled to the display and the memory, the at least one processor being configured:
      to produce and display visual stimuli on a display of a computerized device of a visual-motor drawing task;
      to digitally measure visual and visual motor responses of an individual subject in response to drawings of the displayed visual stimuli drawn directly on the display of the computerized device by the individual subject to replicate the displayed visual stimuli in a corresponding available space of the display, directly below the displayed visual stimuli to complete the visual-motor drawing task;
      to derive a set of features from the visual and visual motor responses that includes:
      to measure a number of lifts, a contact time, a speed and timing, and an acceleration performed by the individual subject to replicate the displayed visual stimuli and complete the visual-motor drawing task;
      to calculate accelerations as an average change in length of drawn lines over time of a replication;
      to calculate a line consistency according to a variance of the accelerations within the drawn lines of the replication;
      to calculate a scale of the replication relative to the displayed visual stimuli;
      to calculate a rotation according to a minimum value of a rotational transformation of keypoints between the replication and the displayed visual stimuli;
      to calculate non-contiguous marks within and outside a rectangular area occupied by ninety percent of the pixels of the replication and less than a predetermined percentage of a length of a longest contiguous mark;
      to train a machine learning model to classify and categorize the digitally measured visual and visual motor responses using the derived set of features;
      to identify parameters of the profile analysis of the interpretive framework corresponding to the parameters of the trained machine learning model;
      to classify and categorize, using the trained machine learning model, the digitally measured visual and visual motor responses of the individual subject to the displayed visual stimuli according to the derived set of features;
      to recognize a pattern of performance errors associated with the individual subject in response to the displayed visual stimuli corresponding to at least one condition based on the classification and categorization, wherein the at least one condition includes a psychological disorder or a neurological disorder; and
      to continually modify parameters of the profile analysis of the interpretive framework corresponding to the parameters of the trained machine learning model for the at least one condition based at least in part on the pattern of performance errors.

10. The apparatus of claim 9, in which the at least one processor is further configured to continually modify the parameters by establishing a baseline for the parameters of the profile analysis of the interpretive framework corresponding to the at least one condition based at least in part on an analysis of the pattern of performance errors determined during the classifying and categorizing of the digitally measured visual and visual motor responses of the individual subject when the individual subject does not suffer from the at least one condition.

11. The apparatus of claim 9, in which the at least one processor is further configured to continually modify the parameters by adjusting the parameters of the profile analysis of the interpretive framework corresponding to the at least one condition based at least in part on an analysis of the pattern of performance errors determined during the classifying and categorizing of the digitally measured visual and visual motor responses of the individual subject when the individual subject suffers from the at least one condition.

12. The apparatus of claim 9, in which the at least one processor is further configured to continually modify the parameters by identifying strengths and weaknesses in visual, motor and/or visual-motor functioning of the individual subject in response to the visual stimuli displayed on the display.

13. The apparatus of claim 9, in which to continually modify the at least one processor is further configured:
   to adjust the parameters of the profile analysis of the interpretive framework corresponding to the at least one condition based at least in part on an analysis of the pattern of performance errors determined during the classifying and categorizing of the digitally measured visual and visual motor responses of the individual subject; and
   to provide an assessment of the individual subject based at least in part on a score of a condition correlation function corresponding to the analysis of the pattern of performance errors determined from the digitally measured visual and visual motor responses of the individual subject.

14. The apparatus of claim 13, in which the at least one processor is further configured to predict a potential condition of the individual subject when the score of the condition correlation function corresponding to the analysis of the pattern of performance errors determined from the digitally measured visual and visual motor responses of the individual subject is within a predetermined range.

15. The apparatus of claim 9, in which the at least one processor is further configured to continually modify the parameters by updating a condition correlation function corresponding to the at least one condition according to the classifying and categorizing of the digitally measured visual and visual motor responses of the individual subject when the individual subject suffers from the at least one condition.

16. A computer program product for improving a profile analysis of an interpretive framework stored in a memory, the computer program product comprising:
- a non-transitory computer readable medium having program code recorded thereon, the program code configured:
  - to produce and display visual stimuli on a display of a computerized device of a visual-motor drawing task;
  - to digitally measure visual and visual motor responses of an individual subject in response to drawings of the displayed visual stimuli drawn directly on the display of the computerized device by the individual subject to replicate the displayed visual stimuli in a corresponding available space of the display, directly below the displayed visual stimuli to complete the visual-motor drawing task;
  - to derive a set of features from the visual and visual motor responses that includes:
    - to measure a number of lifts, a contact time, a speed and timing, and an acceleration performed by the individual subject to replicate the displayed visual stimuli and complete the visual-motor drawing task;
    - to calculate accelerations as an average change in length of drawn lines over time of a replication;
    - to calculate a line consistency according to a variance of the accelerations within the drawn lines of the replication;
    - to calculate a scale of the replication relative to the displayed visual stimuli;
    - to calculate a rotation according to a minimum value of a rotational transformation of keypoints between the replication and the displayed visual stimuli;
    - to calculate non-contiguous marks within and outside a rectangular area occupied by ninety percent of the pixels of the replication and less than a predetermined percentage of a length of a longest contiguous mark;
  - to train a machine learning model to classify and categorize the digitally measured visual and visual motor responses using the derived set of features;
  - to identify parameters of the profile analysis of the interpretive framework corresponding to the parameters of the trained machine learning model;
  - to classify and categorize, using the trained machine learning model, the digitally measured visual and visual motor responses of the individual subject to the displayed visual stimuli according to the derived set of features;
  - to recognize a pattern of performance errors associated with the individual subject in response to the displayed visual stimuli corresponding to at least one condition based on the classification and categorization, wherein the at least one condition includes a psychological disorder or a neurological disorder; and
  - to continually modify parameters of the profile analysis of the interpretive framework corresponding to the parameters of the trained machine learning model for the at least one condition based at least in part on the pattern of performance errors.

17. The computer program product of claim 16, in which the program code is further configured to continually modify the parameters by establishing a baseline for the parameters of the profile analysis of the interpretive framework corresponding to the at least one condition based at least in part on an analysis of the pattern of performance errors determined during the classifying and categorizing of the digitally measured visual and visual motor responses of the individual subject when the individual subject does not suffer from the at least one condition.

18. The computer program product of claim 16, in which the program code is further configured to continually modify the parameters by adjusting the parameters of the profile analysis of the interpretive framework corresponding to the at least one condition based at least in part on an analysis of the pattern of performance errors determined during the classifying and categorizing of the digitally measured visual and visual motor responses of the individual subject when the individual subject suffers from the at least one condition.

19. The computer program product of claim 16, in which the program code is further configured:
- to adjust the parameters of the profile analysis of the interpretive framework corresponding to the at least one condition based at least in part on an analysis of the pattern of performance errors determined during the classifying and categorizing of the digitally measured visual and visual motor responses of the individual subject; and
- to provide an assessment of the individual subject based at least in part on a score of a condition correlation function corresponding to the analysis of the pattern of performance errors determined from the digitally measured visual and visual motor responses of the individual subject.

20. The computer program product of claim 19, in which the program code is further configured to predict a potential condition of the individual subject when the score of the condition correlation function corresponding to the analysis of the pattern of performance errors determined from the digitally measured visual and visual motor responses of the individual subject is within a predetermined range.

21. The computer program product of claim 19, in which the program code is further configured to eliminate at least one potential condition based at least in part on the score of the condition correlation function corresponding to the analysis of the pattern of performance errors determined from the digitally measured visual and visual motor responses of the individual subject.

* * * * *